US008604425B2

(12) United States Patent
Kanda et al.

(10) Patent No.: US 8,604,425 B2
(45) Date of Patent: *Dec. 10, 2013

(54) SAMPLE PRETREATMENT APPARATUS AND MASS SPECTROMETER PROVIDED WITH THE SAME

(71) Applicant: Hitachi High-Technologies Corporation, Tokyo (JP)

(72) Inventors: Katsuhiro Kanda, Hitachinaka (JP); Makoto Nogami, Tsuchiura (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,630

(22) Filed: Nov. 19, 2012

(65) Prior Publication Data

US 2013/0075603 A1 Mar. 28, 2013

Related U.S. Application Data

(63) Continuation of application No. 13/146,802, filed as application No. PCT/JP2010/051094 on Jan. 28, 2010, now Pat. No. 8,319,179.

(30) Foreign Application Priority Data

Jan. 29, 2009 (JP) .................................. 2009-017458

(51) Int. Cl.
*G01N 1/10* (2006.01)
*G01N 1/28* (2006.01)
*G01N 1/02* (2006.01)
*G01N 33/48* (2006.01)
*H01J 49/26* (2006.01)

(52) U.S. Cl.
USPC ............. 250/288; 250/281; 250/428; 422/63; 422/68.1; 435/287.3; 73/864.91; 73/61.59

(58) Field of Classification Search
USPC ................... 250/288, 281, 428; 422/68.1, 63; 73/61.59, 864.91; 435/287.3
See application file for complete search history.

(56) References Cited

U.S. PATENT DOCUMENTS

| 4,862,932 A | 9/1989 | Feinstein et al. |
| 5,350,520 A | 9/1994 | Kikumoto |

(Continued)

FOREIGN PATENT DOCUMENTS

| JP | 02-022557 A | 1/1990 |
| JP | 04-329356 A | 11/1992 |

(Continued)

OTHER PUBLICATIONS

Chinese Office Action received in Chinese Application No. 201080005881.6 dated Dec. 19, 2012.

*Primary Examiner* — Nikita Wells
(74) *Attorney, Agent, or Firm* — Mattingly & Malur, PC

(57) ABSTRACT

The present invention relates to a pretreatment apparatus that performs concentration and separation of a sample, and in particular, in order to provide a sample pretreatment apparatus using a solid-phase extraction column, and a mass spectrometer using the same, which is particularly suitable for clinical analysis in which qualitative/quantitative analysis of a biological sample such as blood is performed, according to each operational step for a solid-phase extraction treatment, for example, a collection device serving as flow passages or containers for collection of waste liquid or extracted matter is installed on a bottom face of the solid-phase extraction column, and the extracted matter is separately collected without being mixed with waste liquid by switching the positions of the collection device.

13 Claims, 11 Drawing Sheets

(56) References Cited

U.S. PATENT DOCUMENTS

| | | |
|---|---|---|
| 5,660,792 A | 8/1997 | Koike |
| 8,012,745 B2 * | 9/2011 | Glezer et al. ............... 435/288.7 |
| 8,319,179 B2 * | 11/2012 | Kanda et al. ................. 250/288 |
| 2011/0201099 A1 | 8/2011 | Anderson et al. |
| 2012/0079875 A1 * | 4/2012 | Nogami et al. .............. 73/61.59 |
| 2012/0121464 A1 * | 5/2012 | Nogami et al. .............. 422/68.1 |

FOREIGN PATENT DOCUMENTS

| | | |
|---|---|---|
| JP | 06-138115 A | 5/1994 |
| JP | 8-164302 A | 6/1996 |
| JP | 11-201953 A | 7/1999 |
| JP | 2000-214148 A | 8/2000 |
| JP | 2006-007081 A | 1/2006 |
| JP | 2007-304078 A | 11/2007 |

* cited by examiner

705

706

707

708

702
701
703
704

709

710

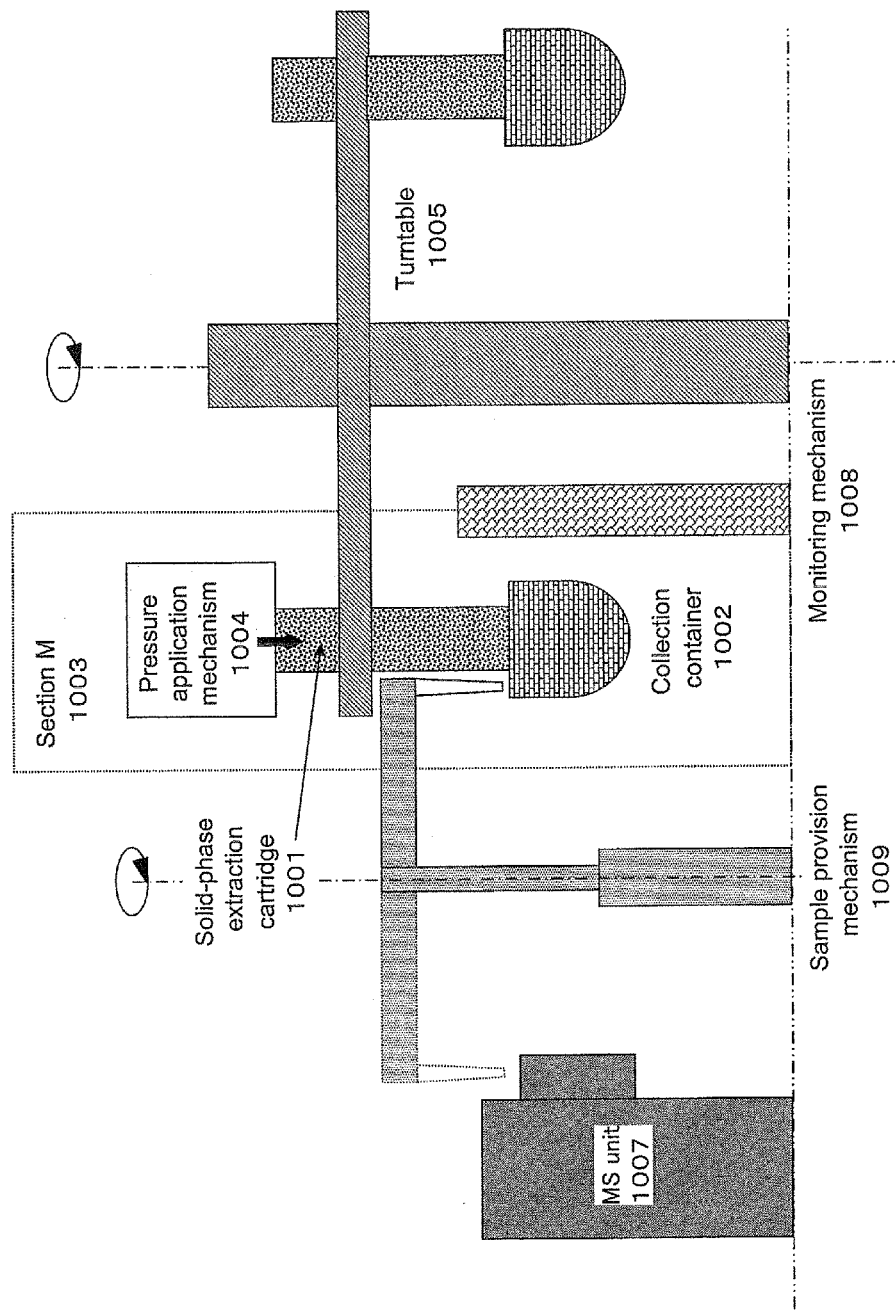

SAMPLE PRETREATMENT APPARATUS AND MASS SPECTROMETER PROVIDED WITH THE SAME

CROSS REFERENCE TO RELATED APPLICATION

This application is a continuation of U.S. patent application Ser. No. 13/146,802, filed Jul. 28, 2011, now U.S. Pat. No. 8,319,179, which is a 371 of international Appl. No. PCT/JP2010/051094, filed Jan. 28, 2010 and which claims priority to Japanese Application No. 2009-017458, filed Jan. 29, 2009.

TECHNICAL FIELD

The present invention relates to a pretreatment apparatus for pretreating a biological sample, such as blood or urine, and amass spectrometer provided with the same, and in particular to a pretreatment apparatus using a solid-phase extraction column, and a mass spectrometer using the same.

BACKGROUND ART

As a method for performing qualitative/quantitative analysis of a biological sample, such as blood or urine, two representatives are a colorimetric analysis that uses a reagent which reacts with a component to be measured in the sample to result in color change, and measures the color change by a photometer, and an immunoassay that adds labels directly or indirectly to a substance which binds specifically to a component to be measured, and counts the labels. In recent years, analysis of a biological sample performed by a physico-chemical method using a mass analyzer has been attempted, and the scope of application thereof is expected to increase in the future.

To examine/analyze a component contained in an organism-derived sample, such as blood, blood serum, blood plasma, cell tissue, or urine, it is difficult to achieve detection at high accuracy, if many kinds of components are simultaneously measured, since many components of more than several tens of thousands of kinds coexist in biological components. Therefore, it is preferred that a pretreatment for concentrating/purifying a biological sample be performed. To subject a low-molecular compound, such as a drug, to laboratory analysis using a mass spectrometer, liquid chromatography (LC) is commonly performed as the pretreatment to separate a target component. Simpler methods for extracting a component are liquid-liquid extraction and solid-phase extraction techniques. In a typical solid-phase extraction technique, the target component is adsorbed to an adsorbent having various properties that is filled in a syringe-like or plate-like container. After washing and removing impurities from the adsorbed components, the target component is eluted and collected from the adsorbent. As compared with the LC separation, the solid-phase extraction method is inferior in component separation performance, but can collect a target component in a short time and with low cost.

To perform the treatment of solid-phase extraction, not only a solid-phase extraction column or plate but also a container for collecting an extracted component is required. In particular, to automate the treatment of solid-phase extraction for the purpose of clinical analysis or the like, it is required to switch collection containers or flow passages according to an operational step so that waste liquid generated in the treatment of solid-phase extraction and extracted matter can be segregated. For example, to apply a turntable system, which is applied to a common automatic immunoassay analyzer or the like, to an automatic apparatus for the treatment of solid-phase extraction, a problem is how to simply achieve segregational collection of waste liquid and extracted matter.

Collection of extracted matter is commonly performed by a fraction collector. The fraction collector is an apparatus to obtain (fractionate) different substances in different containers by utilizing the fact that a period of time of elution of a substance when the substance passes through a column of a liquid chromatography depends on physical/chemical properties of the substance. That is, the apparatus adopts such a mechanism that collection containers are preliminarily arranged on the fraction collector, and collections of waste liquid and extracted matter are performed with a certain timing (for example, a period of time, or the number of drops) (see Patent Documents 1 to 5).

Further, an apparatus for automating a solid-phase extraction treatment is commercially available (see Patent Document 6). Such an apparatus is used, for example, for high-throughput screening of a candidate drug in the field of drug discovery, or the like. Therefore, a solid-phase extraction device used in this apparatus has a plate-like shape, such as a 96 well plate, where independent solid-phase extractions in individual wells are performed simultaneously for all the wells in a plate.

PRIOR ART DOCUMENTS

Patent Documents

Patent Document 1: Japanese Patent Application Laid-Open Publication No. 04-329356
Patent Document 2: Japanese Patent Application Laid-Open Publication No. 2007-304078
Patent Document 3: Japanese Patent Application Laid-Open Publication No. 02-022557
Patent Document 4: Japanese Patent Application Laid-Open Publication No. 2000-214148
Patent Document 5: Japanese Patent Application Laid-Open Publication No. 06-138115
Patent Document 6: Japanese Patent Application Laid-Open Publication No. 2006-7081

DISCLOSURE OF THE INVENTION

Problems to be Solved by the Invention

Since the fraction collector requires a turntable on which a plurality of containers, into which fractionated samples are distributed, is arranged, the apparatus becomes large in size. Further, it is postulated that the number of kinds of samples to be treated is one per one analysis, and that the number of treatment columns is also one.

On the other hand, in a clinical analysis, since it is required to analyze samples/specimens taken from a plurality of patients concurrently and it is required to perform a plurality of solid-phase extraction treatments using a plurality of solid-phase extraction columns, such a large-scale apparatus as a fraction collector cannot deal with these requirements.

Further, in the apparatus for automating a solid-phase extraction treatment, according to each step of solid-phase extraction (for example, extraction agent conditioning, sample provision, impurity wash, or adsorbed component elution), all the wells on the plate are subjected to the same step at the same timing. Therefore, waste liquid disposal (extraction agent conditioning, sample provision, impurity wash) and eluted substance collection (absorbed component elution) cannot be switched independently for each well. This becomes a factor in reducing cost-efficient performance, because of lack of the ability to randomly analyze examination items and randomly analyze various specimens, which is required, for example, in clinical analysis or the like, or because of occurrence of an unused well in a plate when the number of samples is less than that of wells in a plate.

A preferred aim of the present invention is to provide a sample pretreatment apparatus using a solid-phase extraction column, and a mass spectrometer using the same, which are in particular suitable for clinical analysis.

Means for Solving the Problems

The present invention relates to a technique to collect an extracted matter separately without mixing with a waste liquid, according to each operational step for a solid-phase extraction treatment, by disposing, for example, a collection device serving as flow passages or containers for collections of waste liquid and extracted matter on a bottom face of a solid-phase extraction column, and by switching the positions of the collection device to collect the extracted matter separately without mixing with the waste liquid. This collection device can be either of two types, an integrated type or a separate type, where the types are defined in relation to the solid-phase extraction column. The integrated type suggests a cartridge in which a collection device has been preliminarily connected to the bottom face of the solid-phase extraction column. On the other hand, the separate type suggests a mechanism that a collection device is not preliminarily connected to the bottom face of the solid-phase extraction column, but moves to the bottom face of the solid-phase extraction column when needed, where the collection device may be attached to or detached from the solid-phase extraction column, or the collection device may be disposed in another device (for example, a turntable) installed below a device (for example, a turntable) in which the solid-phase extraction column is disposed. Further, a valve mechanism may be installed in a discharge port of the solid-phase extraction column, and a structure that performs switching between flow passages for waste liquid and for extracted matter (for example, a slit) may be included.

Effects of the Invention

According to the present invention, it becomes possible to easily segregate and collect waste liquid and extracted matter without mixing the waste liquid and the extracted matter in automation of the solid-phase extraction treatment.

Further, in the apparatus for automating a solid-phase extraction treatment, a plurality of solid-phase extraction columns on a turntable can be provided to different treatment steps from each other unlike the respective solid-phase extraction wells in the 96 well plate, where the same treatment steps are provided.

BRIEF DESCRIPTIONS OF THE DRAWINGS

FIG. 12 is a side view of the system configuration of a solid-phase extraction treatment according to the integrated type.

BEST MODE FOR CARRYING OUT THE INVENTION

Figure 1:
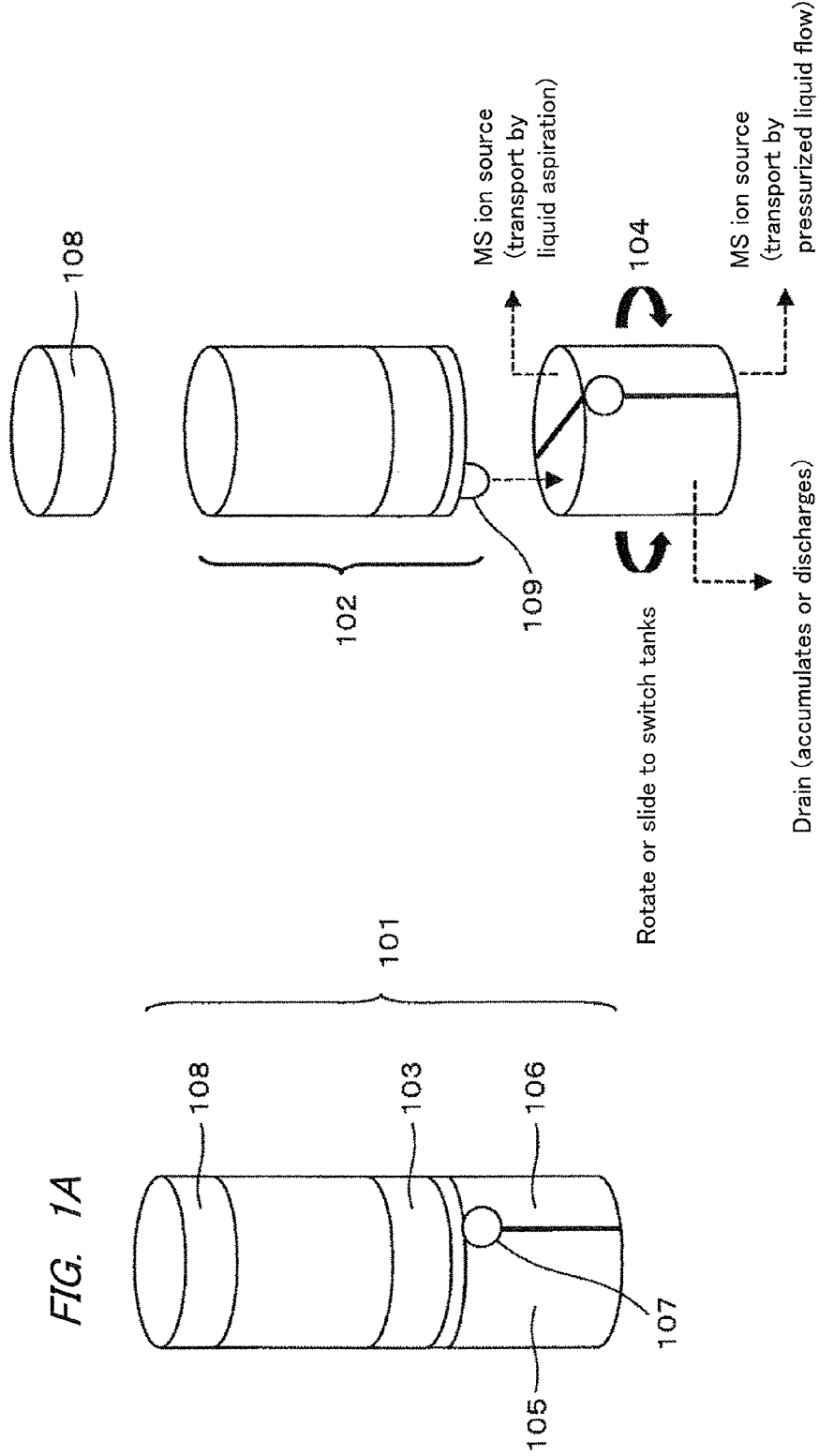
FIGS. 1A and 1B are diagrams for describing a configuration of a solid-phase extraction cartridge.

Embodiments of the present invention will be described in further detail with reference to the drawings. However, the present invention is not limited to the following embodiments. Note that, for convenience of understanding, identical members may be denoted by different reference numerals among the drawings.

First Embodiment

In a first embodiment, a pretreatment apparatus using an integrated type solid-phase extraction cartridge will be described. The integrated type solid-phase extraction cartridge is characterized in that, as a cartridge, it encompasses a mechanism of a solid-phase extraction column and a mechanism of waste liquid and extracted matter collection.

FIG. 1 shows a cartridge used in a solid-phase extraction treatment. As shown in FIGS. 1A and 1B, a cartridge 101 has a collection device 104 on a bottom face of a solid-phase extraction column 102. The collection device (a tray mechanism) 104 is provided with a container or a flow passage for collecting waste liquid or extracted matter generated at each operational step for solid-phase extraction. The collection device 104 is of an integrated type with the solid-phase extraction column 102. The integrated type suggests a cartridge in which a collection device has been preliminarily connected to a bottom face of the solid-phase extraction column 102.

A discharge port 109 from the solid-phase extraction column 102 is at a single site, and therefore the collection device 104 on the bottom face of the solid-phase extraction column 102 has a structure in which, for example, when using a switching mechanism of a rotary type about a center of the bottom face, the position of the discharge port is deviated from the center so that, when switching is performed between a section 105 for waste liquid disposal (a container or a flow passage) and an extracted matter collection tank 106, waste liquid and extracted matter are prevented from mixing. Note that, in FIG. 1A, the reference numeral 103 denotes an extraction agent.

That is, the solid-phase extraction cartridge 101 of this integrated type can avoid scattering of waste liquid and extracted matter to prevent contamination, since a collection container and a waste liquid container are brought into contact with the portion of the discharge port 109 of the solid-phase extraction column 102.

On the other hand, when the collection device 104 is of a slide type or a separate type, the position of the discharge port 109 of the solid-phase extraction column 102 does not matter, and it may be at the center of the column bottom face. Further, as an option in this case, for example, the collection device 104 may have a structure in which only the waste liquid disposal part is not composed of a container, where the waste liquid is discharged into a drain disposed in another part of an apparatus main body.

Figure 3:
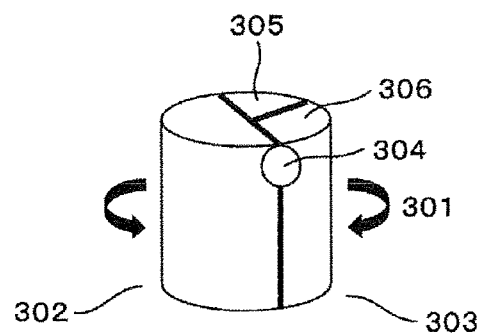
FIG. 3 is a diagram for describing a configuration of a collection device.

Elution of a target component captured in the solid-phase extraction column 102 may be performed not only once but also plural times as an application similar to solid-phase separation. Therefore, as shown in FIG. 3, a collection device 301 has at least one or more extracted matter collection tanks 303 (in an example shown in the figure, an extracted matter collection tank A 305 and an extracted matter collection tank B 306). Note that, in FIG. 3, the reference numeral 302 denotes a waste liquid disposal section.

Figure 4A:
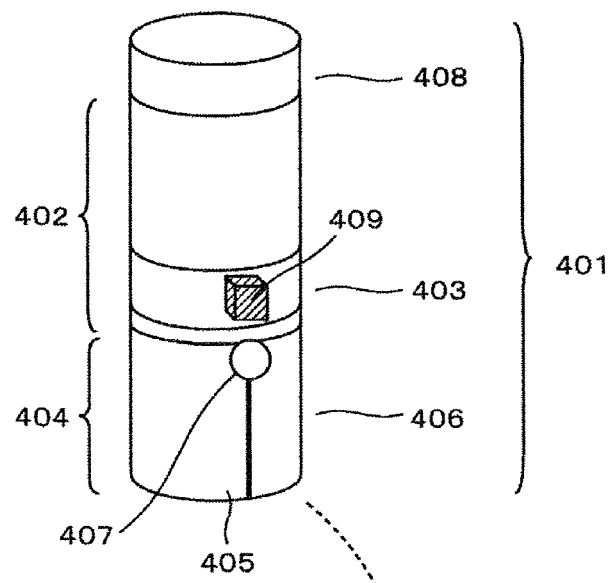
FIGS. 4A and 4B are diagrams for describing a positioning structure of the collection device in FIG. 3.

In the apparatus, as shown in FIG. 4A, since a cartridge 401 in which a solid-phase extraction column 402 and a collection device 404 have been integrated with each other in advance is required to be disposed with good orientation at a predetermined position in a rack for storage or in a device for performing a treatment (for example, a turntable), it has a structure for positioning (a cartridge holding portion, with a recess or a projection, for example) 409.

Figure 4B:
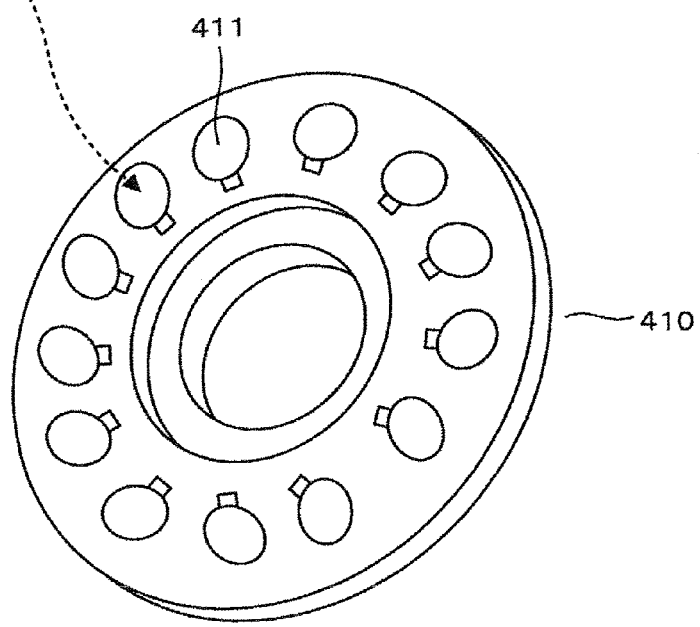

The collection device 404 has a structure in which position switching is performed concordant with the position of the discharge port of the solid-phase extraction column. For example, when using the integrated type, in order to perform position switching of the collection device 404 or the solid-phase extraction column 402 (for example, rotation or slide), the collection device is provided with such a structure (for example, a recess or a projection) as connecting or catching of a switching mechanism that is installed in another part of the apparatus main body. Note that, in FIG. 4A, the reference numeral 403 denotes a extraction agent, 405 denotes a waste liquid disposal section, 406 denotes an extracted matter collection tank, 407 denotes a narrow opening for pressure relief, and 408 denotes a pressure holding valve, while, in FIG. 4B, the reference numeral 410 denotes a turntable, and 411 denotes a solid-phase extraction column discharge port, respectively.

Further, in the case where the collection device has been integrated with the solid-phase extraction column, in order to collect waste liquid or extracted matter generated at each operational step for solid-phase extraction, as shown in FIG. 1A and FIG. 3, the collection device 104, 301 has a mechanism (for example, a narrow opening) 107, 304 for relieving pressure (for keeping the collection device at atmospheric pressure).

The extracted matter collected is provided for mass spectrometry. Therefore, the extracted matter collection tank 106, 303 includes a mechanism for transferring extracted matter to mass spectrometry. For example, the mechanism includes an insertion port for inserting an instrument for performing dispensing or an instrument for capturing extracted matter, or a flow passage for moving extracted matter by pressure control (see FIG. 1). In the latter case, in order to prevent functioning of the mechanism for pressure relief provided in the collection device 104, 301 for the purpose of pressure control, a mechanism for closing the narrow opening is included, for example.

Figure 6C:
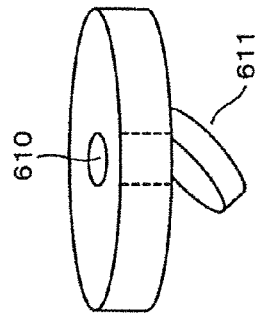
FIGS. 6A to 6D are diagrams for describing a configuration of a pressure holding valve.
Figure 6D:
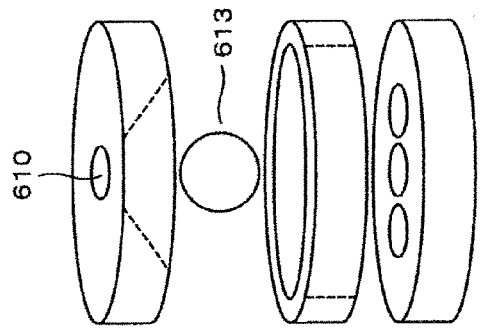
Figure 6B:
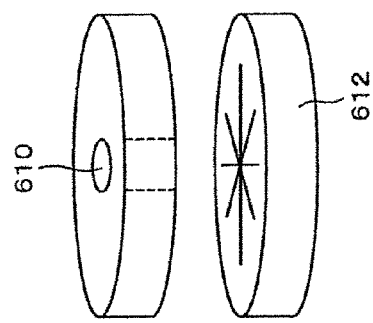
Figure 6A:
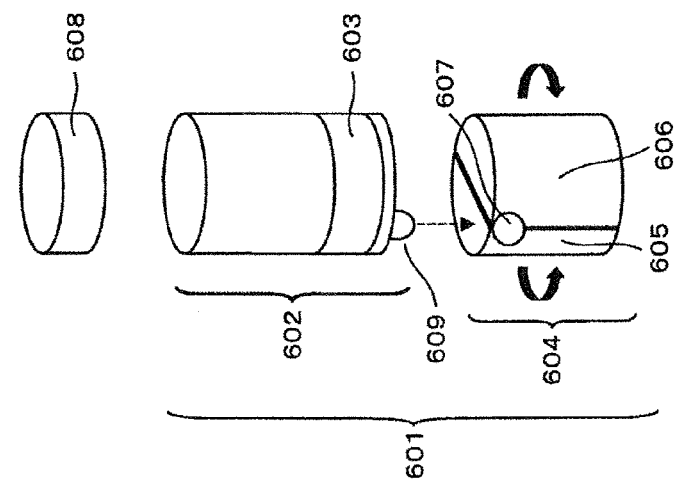

If necessary, in order to hold a state of pressurization at each operational step for solid-phase extraction, as shown in FIG. 1 and FIG. 6A, a pressure holding valve 108, 608 is installed on an upper face of the column, so that flows of various solvents can be facilitated.

Within another part of the apparatus main body, a mechanism for switching mutual position (a mechanism for switching sections) between the solid-phase extraction column 102, 602 and the collection device 104, 604 is provided. According to the integrated type, a disk, an arm, or the like that, for example, rotates or slides the solid-phase extraction column 102, 602 or the collection device 104, 604 to perform position switching is provided. Note that, in FIG. 6A, the reference numeral 601 denotes a solid-phase extraction cartridge, 603 denotes an extraction agent, 605 denotes a waste liquid disposal section, 606 denotes an extracted matter collection tank, 607 denotes a narrow opening for pressure relief, and 609 denotes a solid-phase extraction column discharge port, respectively. Further, in FIGS. 6B to 6D, the reference numeral 610 denotes a narrow opening for introducing pressure, a sample, a reagent, or the like, 611, 612 denote check valves, and 613 denotes a check ball, respectively.

The cartridge after the solid-phase extraction treatment can be detached from the turntable by a collection arm, and stored or disposed of. When remeasuring the extracted matter, the cartridge stored is disposed in an empty section in the turntable. For example, when the cartridge is controlled using a barcode, the cartridge to be remeasured is automatically identified, and the cartridge is not subjected to every step relating to the solid-phase extraction, but moved to a position where it is loaded to a mass spectrometer (also referred to as an MS unit in the following), and remeasured.

The cartridge during storage may be closed with a lid at an upper end of the cartridge in order to keep the extracted matter from drying if necessary. Even if dried, the extracted matter can be redissolved again in a solvent to be remeasured. A solvent amount added at this time is controlled according to, for example, a value obtained by subtracting a volume consumed for measurement from a monitored value of a liquid level (or a volume) of the extracted matter at a solid-phase extraction step.

Second Embodiment

In a second embodiment, a pretreatment apparatus using a separate type solid-phase extraction cartridge will be described. The separate type solid-phase extraction cartridge is characterized in that, since a solid-phase extraction column and a collection device is separated from each other, both of them are synchronized with each other in a timely manner.

FIG. 1 shows a cartridge used for the solid-phase extraction treatment. This cartridge 101 includes the collection device 104 on a bottom face of the solid-phase extraction column, as described in the first embodiment, and the collection device 104 is provided with a container or a flow passage for collecting waste liquid or extracted matter generated at each operational step for solid-phase extraction. This collection device 104 may be of a separate type. The separate type suggests a mechanism that a collection device is not preliminarily connected to the bottom face of the solid-phase extraction column 102, but moves to the bottom face of the solid-phase extraction column when needed, where the collection device 104 may be attached to and detached from the solid-phase extraction column 102, or the collection device 104 may be disposed in a device (for example, a turntable) installed below another device (for example, a turntable) in which the solid-phase extraction column 102 is disposed.

The discharge port 109 from the solid-phase extraction column 102, which is at a single site, may be placed at the center of the bottom surface of the solid-phase extraction column, because, as described in the first embodiment, the position of the discharge port 109 in relation to the solid-phase extraction column 102 does not matter, when the collection device 104 is of the separate type. Further, as an option in this case, for example, the collection device 104 may have a structure in which, only the waste liquid disposal part is not composed of a container, and may have a structure in which the waste liquid is discharged into a drain installed within another part of the apparatus main body.

Like the case of the integrated type, elution of a target component captured in the solid-phase extraction column may be performed not only once but also plural times as an application similar to solid-phase separation. Therefore, the collection device 301 has at least one or more extracted matter collection tanks 305, 306 (see FIG. 3).

In the apparatus, if the solid-phase extraction column 402 and the collection device 404 are required to be disposed with good orientation at predetermined positions in a rack for storage or a device for performing a treatment (for example, a turntable), a structure for positioning (for example, a recess or a projection) 409 is provided (see FIG. 4).

The collection device has a structure in which position switching is performed concordant with the position of the discharge port of the solid-phase extraction column. For example, according to the separate type, the collection device 404 and a conveyance mechanism placed in the other part of the apparatus main body operate together in a linked manner to move the collection device 404 to below the solid-phase extraction column 402 in accordance with each operational step for solid-phase extraction treatment.

Further, when the collection device is brought into contact with the solid-phase extraction column, in order to collect waste liquid or extracted matter generated at each operational step for solid-phase extraction, the collection device has a mechanism (for example, a narrow opening) for relieving pressure (for keeping the collection device at atmospheric pressure) (see FIGS. 1 and 3).

Like the case of the integrated type, the extracted matter collected is provided for mass spectrometry. Therefore, the extracted matter collection tank includes a mechanism for transferring extracted matter to mass spectrometry. For example, an insertion port for inserting an instrument for performing dispensing or an instrument for capturing extracted matter, or a flow passage for moving extracted matter by pressure control is included (see FIG. 1). In the latter case, in order to prevent functioning of the mechanism for pressure relief installed in the collection device for the purpose of pressure control, a mechanism for closing the narrow opening is included, for example.

For example, in the case of the separate type, it is required to install a waste liquid disposal mechanism and a collection mechanism in another part of the apparatus main body. In this case, switching between the waste liquid disposal part and the collection part is performed as needed using time during treatment steps or the like as guiding parameters. In particular, regarding positioning of the extracted matter collection tank, it does not matter whether a mechanism thereof is of a rotary type, a slide type, or the like, but the collection tank is switched to a specified position (for example, immediately below the discharge port of the solid-phase extraction column) in time with extracted matter collection.

If necessary, in order to hold a state of pressurization at each operational step for solid-phase extraction, a pressure holding valve is installed on an upper face of the column, so that flows of various solvents performed by pressurization can be facilitated (see FIGS. 1 and 6).

In another part of the apparatus main body, a mechanism for switching mutual position between the solid-phase extraction column and the collection device is provided. In the case of the separate type, a disk, an arm, or the like for conveying the collection device to a predetermined position below the solid-phase extraction column is provided, for example.

Figure 7B:
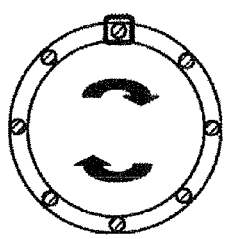
FIGS. 7A to 7G are diagrams for describing a turntable structure for a collection device.
Figure 7C:
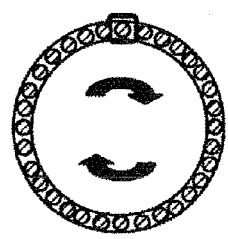
Figure 7D:
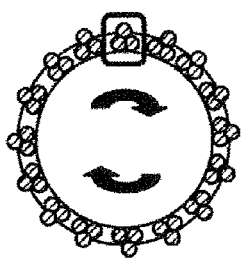
Figure 7E:
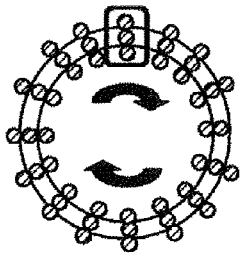
Figure 7A:
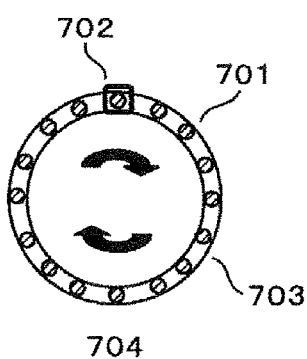
Figure 7F:
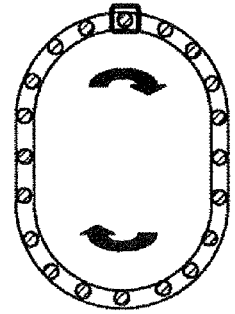
Figure 7G:

Among the separate types, if the collection devices are disposed in a device (for example, a turntable) installed below another device (for example, a turntable) in which the solid-phase extraction column is disposed, as shown in FIGS. 7B to 7G, for example, there are a plurality of patterns of a turntable structure for the part of the collection devices. For example, in one pattern, a waste liquid and extracted matter collection unit is a turntable having the same shape as a turntable 703 for the part of disposing the solid-phase extraction columns in a solid-phase extraction treatment unit 704 shown in FIG. 7A. This pattern further includes a pattern where the total number of disposed collection devices (waste liquid disposal sections and extracted matter collection tanks) is equal to that of solid-phase extraction columns, and other patterns, shown by collection units 705 to 708, where the total number of disposed collections containers are different from that of solid-phase extraction columns, as shown in FIGS. 7B to 7E. Further, for example, as shown in FIGS. 7F and 7G, the collection unit may be a turntable 709, which is different in shape from the turntable for the part of the solid-phase extraction columns. Further, the collection unit may be of a belt shape 710. Note that, in FIG. 7, the reference numeral 701 denotes an insertion portion for a solid-phase extraction column, and 702 denotes a pressure-applying unit, respectively.

Like the case of the integrated type, the cartridge after the solid-phase extraction treatment can be detached from the turntable by a collection arm, and stored or disposed of. When remeasuring the extracted matter, the cartridge stored is disposed in an empty section in the turntable. For example, in a case where the cartridge is barcode-controlled, it is automatically identified, and the cartridge is not subjected to every step relating to the solid-phase extraction, but moved to a position where it is loaded to an MS unit, and remeasured.

The cartridge stored may be closed at a cartridge upper end in order to prevent the extracted matter from drying if necessary.

Even if dried, the extracted matter can be redissolved in solvent to be remeasured. A solvent amount added at this time is controlled according to, for example, a value obtained by subtracting a volume consumed for measurement from a monitored value of a liquid level (or a volume) of the extracted matter at a solid-phase extraction step.

Third Embodiment

In a third embodiment, a pretreatment apparatus using a valve-switching type solid-phase extraction cartridge will be described.

Figure 2:
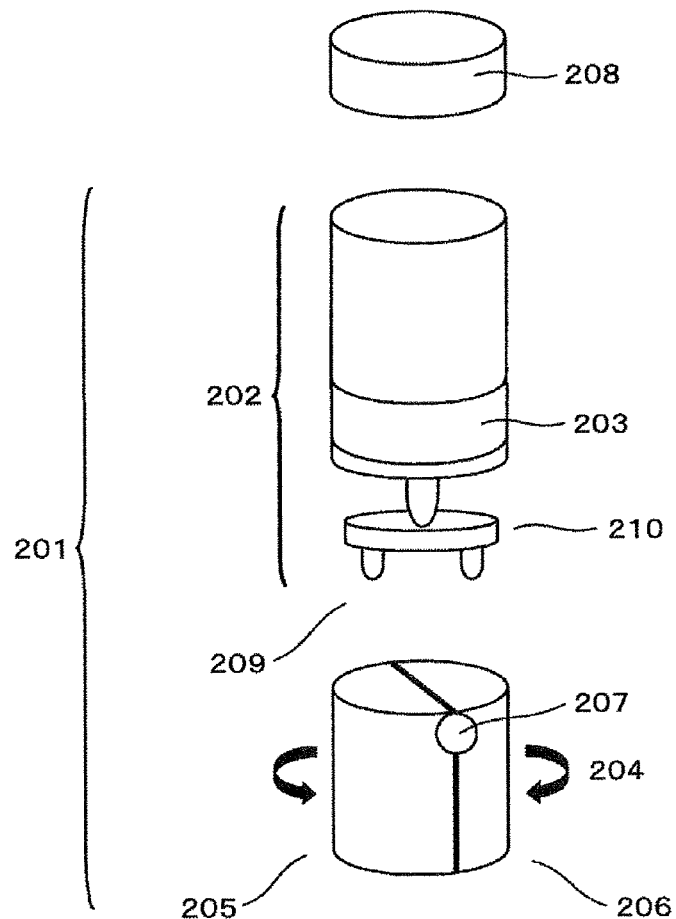
FIG. 2 is a diagram for describing a configuration of a solid-phase extraction cartridge provided with a valve mechanism.

FIG. 2 shows a cartridge used in a solid-phase extraction treatment. As shown in FIG. 2, a cartridge 201 includes a collection device on a bottom face of a solid-phase extraction column 202, like the cartridge 101 shown in FIG. 1. A collection device 204 is provided with a container or a flow passage for collecting waste liquid or extracted matter generated at each operational step for solid-phase extraction. This collection device may be of an integrated type or of a separate type in relation to the solid-phase extraction column 202. The integrated type suggests a cartridge in which a collection device has been preliminarily connected to a bottom face of the solid-phase extraction column 202. On the other hand, the separate type suggests a mechanism that a collection device is not preliminarily connected to the bottom face of the solid-phase extraction column 202, but moves to the bottom face of the solid-phase extraction column when needed, where the collection device is attached to and detached from the solid-phase extraction column 202, or the collection device is disposed in a device (for example, a turntable) installed below another device (for example, a turntable) in which the solid-phase extraction column 202 is disposed.

A discharge port 209 from the solid-phase extraction column 202 is at a single site, and therefore a structure (for example, a slit) may be included that a valve 210 is installed in the discharge port portion 209 of the solid-phase extraction column 202 so that flow passage for waste liquid and extracted matter is switched (see FIG. 2). Note that, in FIG. 2, the reference numeral 203 denotes a extraction agent, 205 denotes a waste liquid disposal section, 206 denotes an extracted matter collection tank, 207 denotes a narrow opening for pressure relief, and 208 denotes a pressure holding valve, respectively.

Like the cartridge 101 shown in FIG. 1, elution of a target component captured in the solid-phase extraction column 202 may be performed not only once but also a plurality of times as a solid-phase separation-like application. Therefore, the collection device has at least one or more extracted matter collection tanks 305, 306 (see FIG. 3).

In the apparatus, if the solid-phase extraction column 402 and the collection device 404, or the cartridge 401 in which both of them have been preliminarily integrated with each other is required to be disposed with good orientation at a predetermined position in a rack for storage or a device for performing a treatment (for example, a turntable), it has the structure for positioning (for example, a recess or a projection) 409 (see FIG. 4).

The collection device may have a structure in which position switching is performed concordant with the position of the discharge port of the solid-phase extraction column. For example, in the case of the integrated type, in order to perform position switching of the collection device 404 or the solid-phase extraction column 402 (for example, rotation, or slide), the collection device is provided with such a structure as connecting or catching of a switching mechanism that is placed in the other part of the apparatus main body (for example, a recess or a projection), as in the first embodiment. On the other hand, in the case of the separate type, like the second embodiment, the collection device 404 and a movement mechanism placed in the other part of the apparatus main body operate together in a linked manner to move the collection device 404 to below the solid-phase extraction column 402 in accordance with each operational step for solid-phase extraction treatment.

Further, like the cartridge 101 shown in FIG. 1, in a case where the collection device is brought into contact with the solid-phase extraction column, in order to collect waste liquid or extracted matter generated at each operational step for solid-phase extraction, the collection device has a mechanism (for example, a narrow opening) for relieving pressure (for keeping the collection device at atmospheric pressure) (see FIGS. 2 and 3).

The extracted matter collected is provided for mass spectrometry. Therefore, the extracted matter collection tank includes a mechanism for transferring the extracted matter to mass spectrometry. For example, an insertion port for inserting an instrument for performing dispensing or an instrument for capturing the extracted matter, or a flow passage for moving the extracted matter by pressure control is included (see FIG. 1). In the latter case, in order to prevent functioning of the mechanism for pressure relief installed in the collection device for the purpose of pressure control, a mechanism for closing the narrow opening is included, for example.

For example, in a case of the separate type, like the cartridge 101 shown in FIG. 1, it is required to install a waste liquid disposal mechanism and a collection mechanism in another part of the apparatus main body. In this case, switching between the waste liquid disposal part and the collection part is performed as needed using time during treatment steps or the like as a guiding parameter. In particular, regarding positioning of the extracted matter collection tank 106, it does not matter whether a mechanism thereof is of a rotary type, a slide type, or the like, but the collection tank is switched to a specified position (for example, immediately below the discharge port of the solid-phase extraction column) in time with extracted matter collection.

If necessary, in order to hold a state of pressurization at each operational step for solid-phase extraction, a pressure holding valve is installed on an upper face of the column, so that flows of various solvents can be facilitated (see FIGS. 2 and 6).

In another part of the apparatus main body, a mechanism for switching the valve (for example, a slit) 210 installed in the discharge port 209 of the solid-phase extraction column 202 is included. Further, a mechanism for switching mutual position between the solid-phase extraction column 202 and the collection device 204 may be included. In a case of the integrated type, a disk, an arm, or the like that, for example, rotates or slides the solid-phase extraction column 202 or the collection device 204 to perform position switching is included. Further, in a case of the separate type, similarly, a disk, an arm, or the like for moving the collection device 204 to a predetermined position below the solid-phase extraction column is included.

Like the cartridge 101 shown in FIG. 1, among the separate types, if the collection devices are disposed in a device (for example, a turntable) disposed below another device (for example, a turntable) provided with the solid-phase extraction column, for example, there are a plurality of patterns of a turntable structure for the part of the collection devices (see FIG. 7). For example, in one pattern, the turntable for the part of the collection device is a turntable having the same shape as a turntable for the solid-phase extraction column, where the number of collection devices (waste liquid disposal sections and extracted matter collection tanks) may be equal to or different from that of solid-phase extraction columns. Further, for example, the turntable for the part of the collection devices may be a turntable having a different shape from the turntable for the solid-phase extraction column, or may be of a belt shape.

Fourth Embodiment

In a fourth embodiment, photometric detection when an extracted matter collection tank is provided with a cuvette structure will be described.

A component subjected to solid-phase extraction may be a component to be measured or a component to be measured that is labeled (for example, fluorescently). Note that, in the latter case, a sample is subjected to a fluorescent labeling treatment before the solid-phase extraction treatment. Note further that, in a case with the fluorescent labeling treatment, a component to be measured may as well be labeled after the solid-phase extraction treatment may be labeled.

Figure 5:
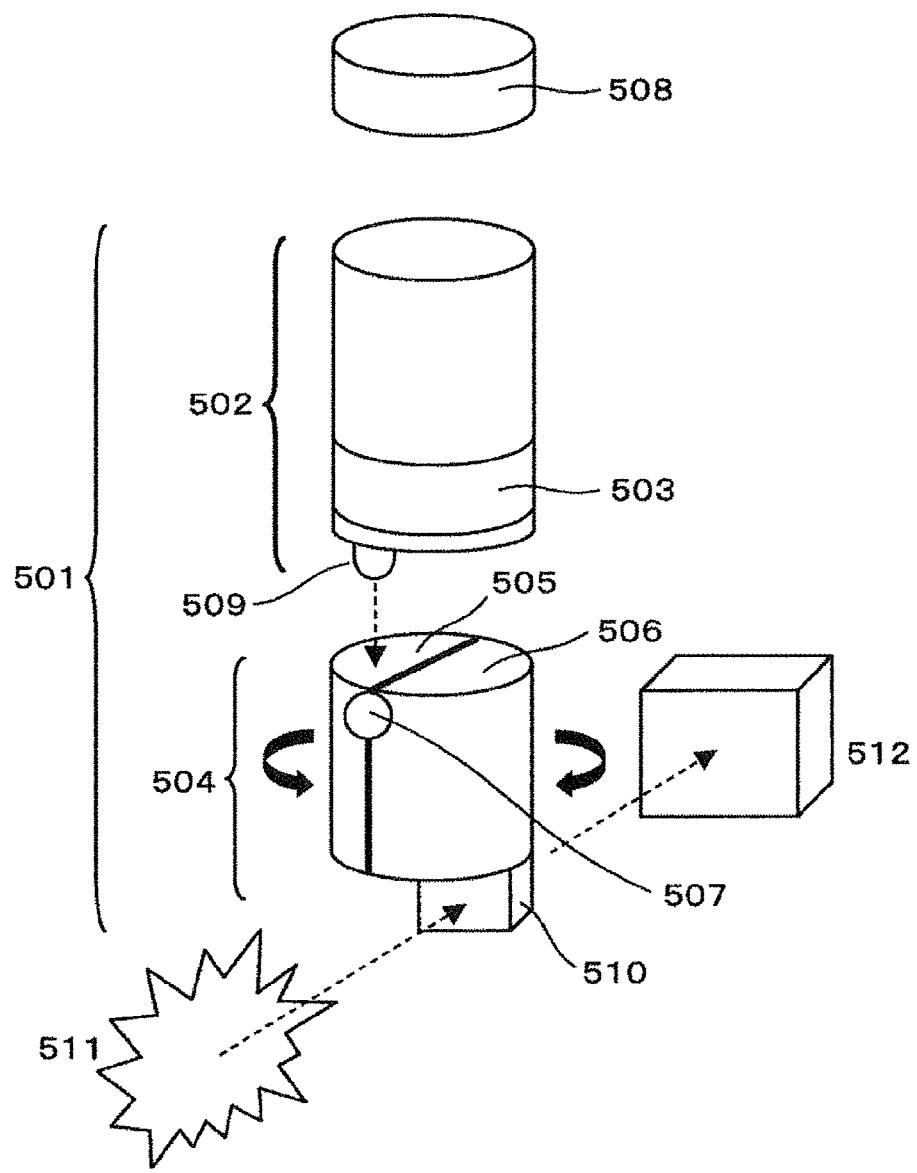
FIG. 5 is a diagram for describing a cuvette structure.

As shown in FIG. 5, extracted matter collected in an extracted matter collection tank 506 stays in the extracted matter collection tank 506 itself, or in a cuvette 510 added structurally thereto (FIG. 5). A photometric detection system 512 detects the extracted matter in the cuvette 510, using a light source 511, thereby performing quantitation of the extracted matter.

Fifth Embodiment

In a fifth embodiment, a system configuration for automating a solid-phase extraction treatment in a case of using the separate type solid-phase extraction cartridge will be described.

Figure 8:
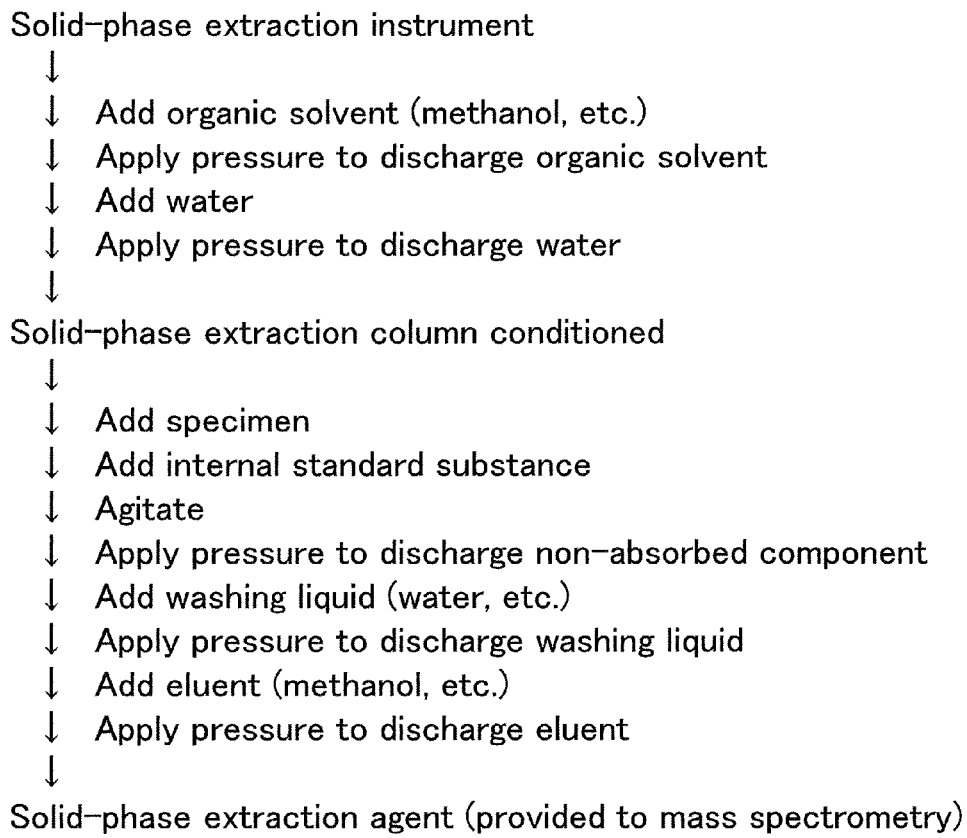
FIG. 8 is a flowchart of a solid-phase extraction treatment.

First, FIG. 8 shows a flowchart of the solid-phase extraction treatment. As shown in FIG. 8, the solid-phase extraction treatment is composed of a conditioning step of a solid-phase extraction agent using an organic solvent and $H_2O$, a sample providing step to the solid-phase extraction agent, a washing and removing step of impurities non-specifically absorbed to the solid-phase extraction agent, an eluting and collecting step of a target component specifically absorbed to the solid-phase extraction agent, and other steps of the like. Extracted matter obtained is provided to, for example, a mass spectrometer, so that it can be used for clinical analysis by performing identification or quantitation of components contained therein.

At each step, in order to let reagents and samples flow through a solid-phase extraction agent, pressure application is performed (implemented by a pressurization treatment on an upstream side of a solid-phase extraction cartridge or a negative pressurization treatment on a downstream side thereof). Among solutions discharged through the solid-phase extraction agent, only a solution obtained at the eluting and collecting step, which is a final step, is collected and provided for analysis, and solutions discharged at respective steps other than the eluting and collecting step are treated as waste liquid.

Figure 9:
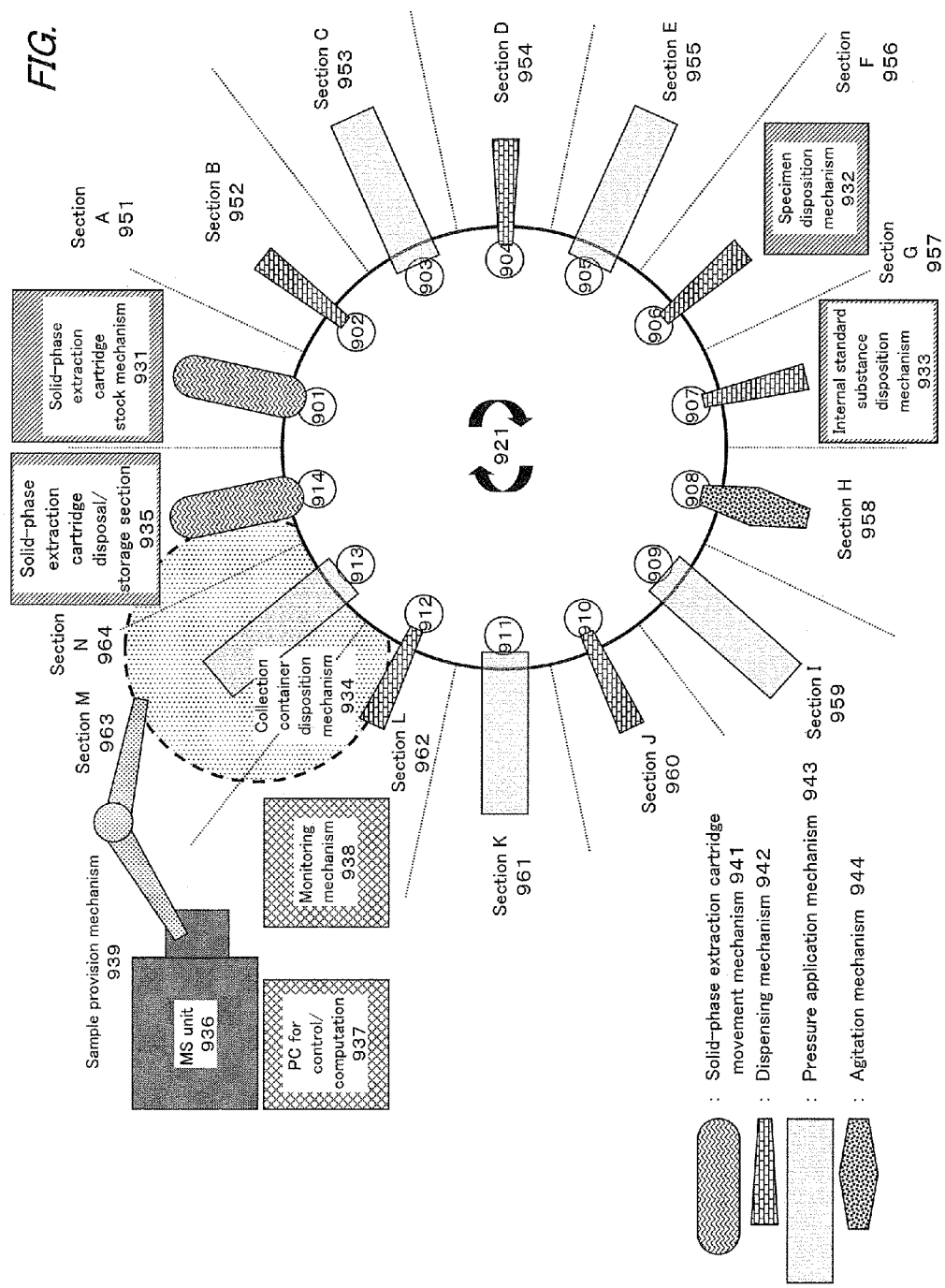
FIG. 9 is a top view of a system configuration of a solid-phase extraction treatment according to a separate type.
Figure 10:
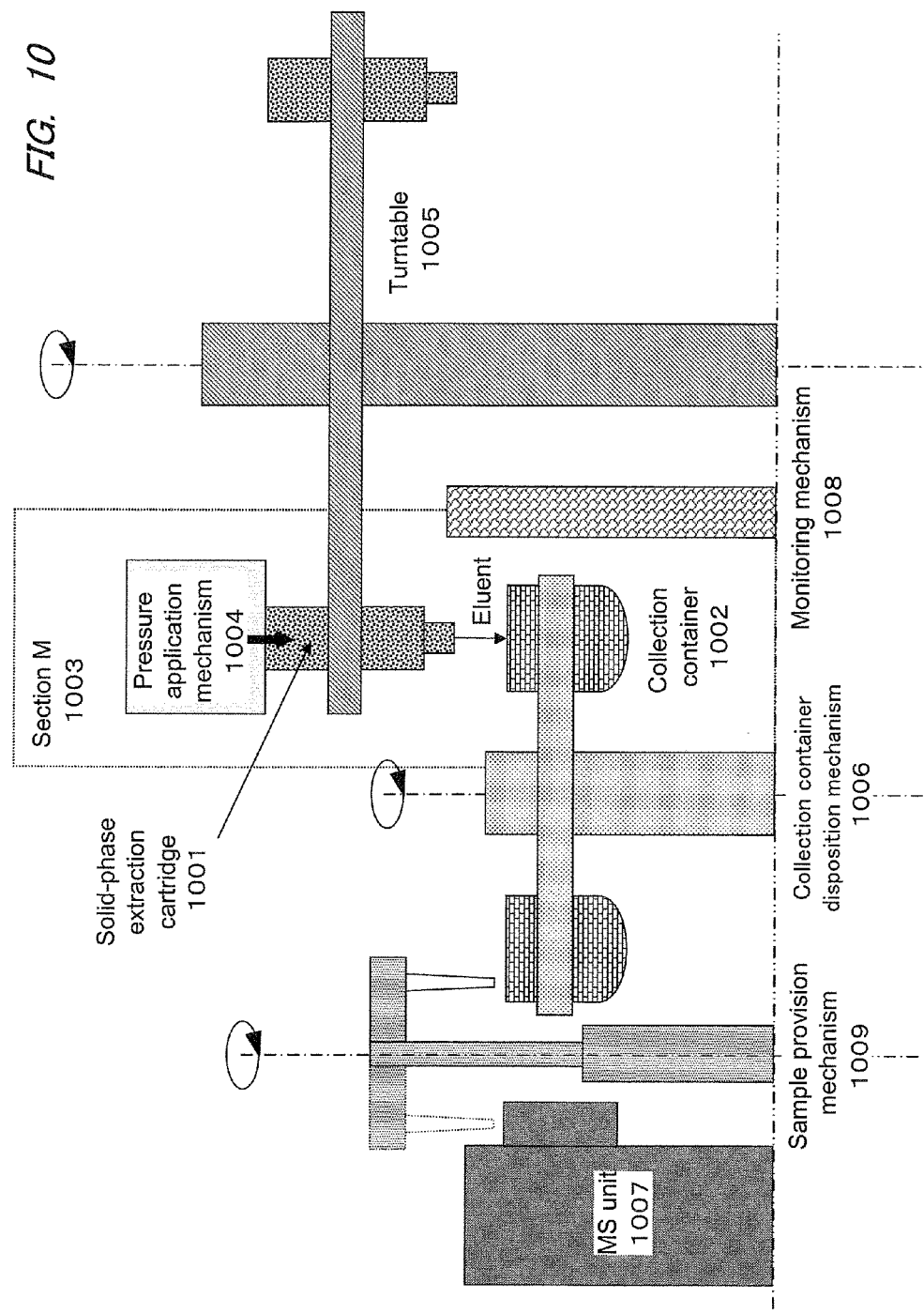
FIG. 10 is a side view of the system configuration of a solid-phase extraction treatment according to the separate type.

FIG. 9 shows an example of a top view of a system configuration for automating a solid-phase extraction treatment using the separate type solid-phase extraction cartridge in which the solid-phase extraction column and the collection device are separated from each other. In order to achieve the ability to randomly analyze examination items and randomly analyze various specimens, which is required in clinical analysis or the like, solid-phase extraction cartridges are arranged in 14 sections concentrically on a turntable (disposed at cartridge holding portions 901 to 914 positioned in sections A to N). Then, such a mechanism that, according to the flowchart shown in FIG. 8, the respective steps composing the solid-phase extraction treatment are sequentially performed along the circular track concentrically in parallel is adopted. Measurement of blood drug concentration will be taken below as an example to describe a specific operational procedure. Note that, as shown in FIGS. 9 and 10, the system is provided with a mechanism 938, 1008 for monitoring conditions of the steps of the treatment, and control of the entire system and computation of data analysis or the like are performed by a PC (personal computer) 937.

First, a solid-phase extraction cartridge movement mechanism 941 conveys one solid-phase extraction cartridge from a solid-phase extraction cartridge stock mechanism 931 to the cartridge holding portion 901 positioned at the section A on the turntable. Note that this solid-phase extraction cartridge is referred to as C1 below for convenience.

Next, a turntable 921, 1005 makes turn in a clockwise direction by an angle corresponding to one section so that C1 moves to the cartridge holding portion 902 positioned in the section B. A conditioning organic solvent dispensing mechanism 942 dispenses a certain amount of organic solvent (for example, 100% methanol) to C1.

Next, the turntable 921, 1005 makes turn in a clockwise direction by an angle corresponding to one section so that C1 moves to the cartridge holding portion 903 positioned in the section C. A pressure application mechanism 943 pressurizes C1, thereby causing organic solvent to wet the solid-phase extraction agent. Waste liquid is disposed of after being collected into a drain, a waste liquid collection container, or the like.

Next, the turntable 921, 1005 makes turn in a clockwise direction by an angle corresponding to one section so that C1 moves to the cartridge holding portion 904 positioned in the section D. A conditioning $H_2O$ dispensing mechanism 942 dispenses a certain amount of $H_2O$ to C1.

Next, the turntable 921, 1005 makes turn in a clockwise direction by an angle corresponding to one section so that C1 moves to the cartridge holding portion 905 positioned in the section E.

The pressure application mechanism 943 pressurizes C1, thereby causing the organic solvent to wet the solid-phase extraction agent. Waste liquid is disposed of after being collected into a drain, a waste liquid collection container, or the like.

Next, the turntable 921, 1005 makes turn in a clockwise direction by an angle corresponding to one section so that C1 moves to the cartridge holding portion 906 positioned in the section F. A specimen dispensing mechanism 942 obtains a certain amount of specimen from a specimen container disposed at a specimen dispensing position of a specimen disposition mechanism 932, and dispenses the same to C1.

Next, the turntable 921, 1005 makes turn in a clockwise direction by an angle corresponding to one section so that C1 moves to the cartridge holding portion 907 positioned in the section G. An internal standard substance dispensing mechanism 942 obtains a certain amount of internal standard substance from an internal standard substance container disposed at an internal standard substance dispensing position of an internal standard substance disposition mechanism 933, and dispenses the same to C1.

Next, the turntable 921, 1005 makes turn in a clockwise direction by an angle corresponding to one section so that C1 moves to the cartridge holding portion 908 positioned in the section H. An agitation mechanism 944 agitates the specimen and the internal standard substance in C1.

Next, the turntable 921, 1005 makes turn in a clockwise direction by an angle corresponding to one section so that C1 moves to the cartridge holding portion 909 positioned in the section I. The pressure application mechanism 943 pressurizes C1, thereby causing a mixed solution of the specimen and the internal standard substance to wet the solid-phase extraction agent. Waste liquid is disposed of after collected into a drain, a waste liquid collection container, or the like.

Next, the turntable 921, 1005 makes turn in a clockwise direction by an angle corresponding to one section so that C1 moves to the cartridge holding portion 910 positioned in the section J. A washing liquid dispensing mechanism 942 dispenses a certain amount of washing liquid to C1.

Next, the turntable 921, 1005 makes turn in a clockwise direction by an angle corresponding to one section so that C1 moves to the cartridge holding portion 911 positioned in the section K. The pressure application mechanism 943 pressurizes C1, thereby causing a washing liquid to wet the solid-phase extraction agent. Waste liquid is disposed of after being collected into a drain, a waste liquid collection container, or the like.

Next, the turntable 921, 1005 makes turn in a clockwise direction by an angle corresponding to one section so that C1 moves to the cartridge holding portion 912 positioned in the section L. An eluent dispensing mechanism 942 dispenses a certain amount of eluent to C1.

Next, the turntable 921, 1005 makes turn in a clockwise direction by an angle corresponding to one section so that C1 moves to the cartridge holding portion 913 positioned in the section M. The pressure application mechanism 943 pressurizes C1, thereby causing a washing liquid to wet the solid-phase extraction agent. FIG. 10 shows a side view of the system configuration in the section M. The eluent discharged from a solid-phase extraction cartridge 1001 (C1) is collected in a collection container (a tray mechanism) 1002 that stands by at a position immediately below a discharge port of C1 on a collection container disposition mechanism (which functions as a collection target switching mechanism in the fifth embodiment) 934, 1006. Further, in order to transfer the eluent to a mass spectrometry step, the collection container 1002 that has collected the eluent moves to a predetermined position on the collection container disposition mechanism 934, 1006, and then the eluent is provided to an MS unit 936, 1007 in an on-line or off-line manner to quantitate a target component in the eluent while separating the same from the eluent.

Examples of the off-line sample provision to the MS unit include, for example, that a sample provision mechanism 939, 1009 aspirates and introduces a required amount of sample directly or indirectly (for example, a flow injection system) into an ion source of the MS unit.

Next, the turntable 921, 1005 makes turn in a clockwise direction by an angle corresponding to one section so that C1 moves to the cartridge holding portion 914 positioned in the section N. The solid-phase extraction cartridge movement mechanism 941 collects C1 from the turntable 921, 1005 and disposes of the same into a cartridge disposal portion 935. The cartridge disposal portion 935 can store the cartridge collected for reuse or the like.

The foregoing is a sequence of operations performed on the turntable, and if the turntable 921, 1005 next makes turn in a clockwise direction by an angle corresponding to one section, the cartridge holding portion which is empty after disposal of C1 returns to the section A 951, and one cycle of the solid-phase extraction treatment is completed.

The collection container 1002 after the solid-phase extraction treatment can be detached from the sample provision mechanism 939,1009 by a collection arm, instead of being disposed of, and stored. When remeasuring the extracted matter, the collection container 1002 stored is disposed in an empty portion on the turntable, and, for example, if the collection container is barcode-controlled, it is automatically identified, and the collection container 1002 is moved to a position for loading the same into the MS unit 936, 1007, and remeasurement is performed.

The collection container 1002 stored may be closed at an upper end of the collection container in order to keep the extracted matter from drying if necessary. Even if dried, the extracted matter can be redissolved in solvent to be remeasured. A solvent amount added at that time is controlled according to, for example, a value obtained by subtracting a volume consumed for measurement from a monitored value of a liquid level (or a volume) of the extracted matter at solid-phase extraction step.

Note that, after C1 has moved to the cartridge holding portion 902 positioned at the section B, C2 is charged into an empty cartridge holding portion positioned at the section A, for example, as a new solid-phase extraction cartridge 1001. C2 causes the treatment for a second specimen to start with delay of one section (operation) behind C1. Third and subsequent specimens are treated in the same manner, following C2, and therefore the treatments for 14 specimens corresponding to the number of sections are sequentially performed in parallel on the turntable 921, 1005. Re-examination is also treated in the same manner.

Sixth Embodiment

In a sixth embodiment, a system configuration for automating a solid-phase extraction treatment when the integrated type cartridge is used will be described.

Figure 11:
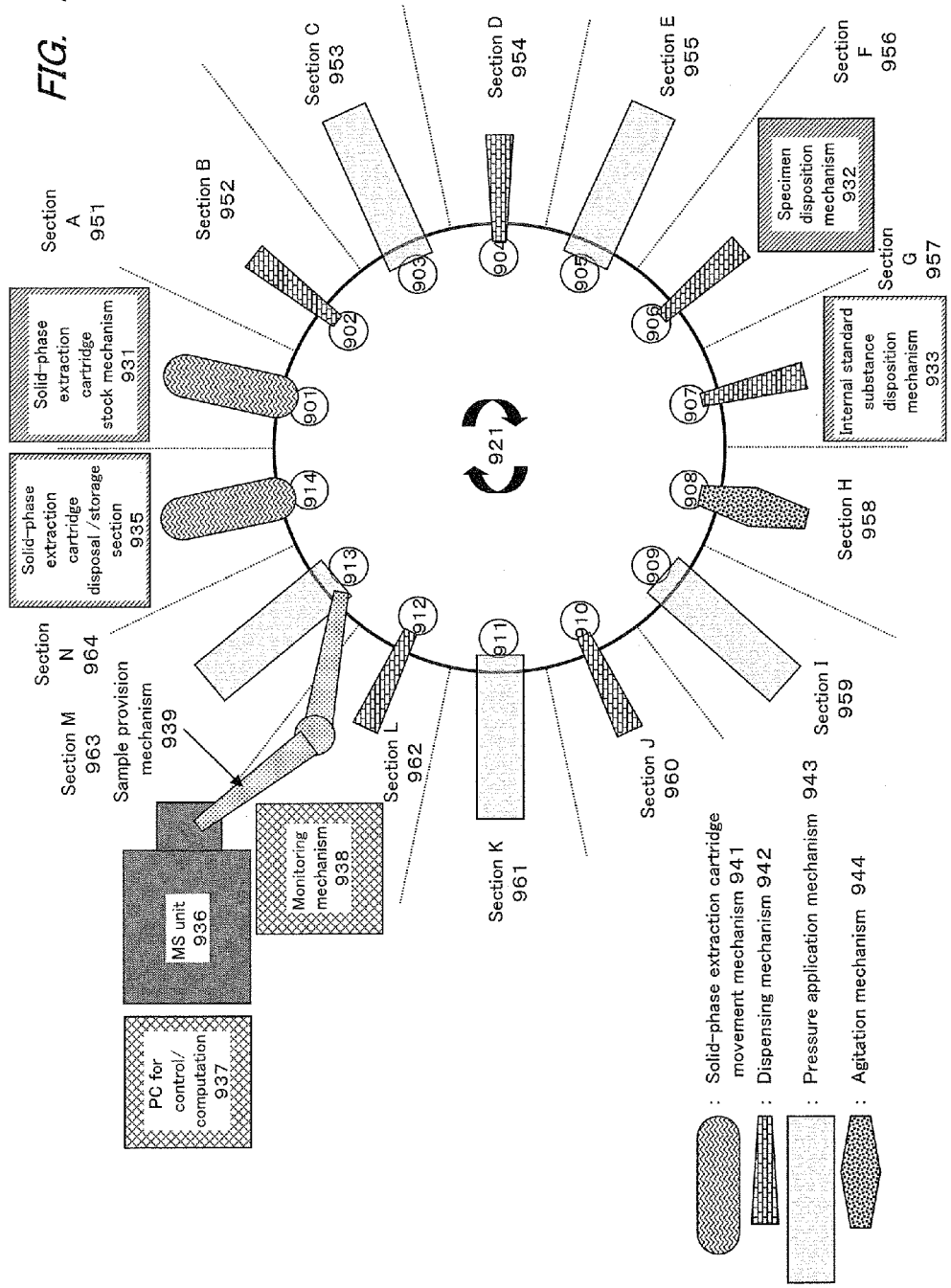
FIG. 11 is a top view of a system configuration of a solid-phase extraction treatment according to an integrated type.

FIG. 11 shows an example of a top view of a system configuration for automating a solid-phase extraction treatment using the integrated type cartridge in which a solid-phase extraction column and a collection device have been connected to each other. In order to achieve the ability to randomly analyze examination items and randomly analyze various specimens, which is required in clinical analysis or the like, for example, like the case of the separate type shown in FIG. 9, solid-phase extraction cartridges are arranged (disposed at the cartridge holding portions 901 to 914 positioned in the sections A to N) in 14 sections concentrically on a turntable (which functions as a collection target switching mechanism in the sixth embodiment). Then, such a mechanism that, according to the flowchart shown in FIG. 8, the respective steps composing the solid-phase extraction treatment are sequentially performed along the circular track concentrically in parallel is adopted. Measurement of blood drug concentration will be taken below as an example to describe a specific operational procedure. Note that, as shown in FIGS. 11 and 12, the system is provided with the mechanism 938, 1008 for monitoring conditions of the steps of the treatment, and control of the entire system and computation of data analysis or the like are performed by the PC 937.

First, the solid-phase extraction cartridge movement mechanism 941 conveys one solid-phase extraction cartridge from the solid-phase extraction cartridge stock mechanism 931 to the cartridge holding portion 901 positioned at the section A on the turntable 921, 1005. At this time, as shown in FIGS. 12 and 1B, a collection device (a collection container) 1002 positioned on a bottom face of the solid-phase extraction column is switched to a waste liquid disposal section (a container or a flow passage) instead of the extracted matter collection tank. This solid-phase extraction cartridge 1001 is referred to as C1 for convenience.

Thereafter, like the case of the separate type, the turntable 921, 1005 makes turn in a clockwise direction by an angle corresponding to one section so that C1 moves to the cartridge holding portion 902 positioned in the section B. The conditioning organic solvent dispensing mechanism 942 dispenses a certain amount of organic solvent (for example, 100% methanol) to C1.

Next, the turntable 921, 1005 makes turn in a clockwise direction by an angle corresponding to one section so that C1 moves to the cartridge holding portion 903 positioned in the section C. The pressure application mechanism 943 pressurizes C1, thereby causing an organic solvent to wet the solid-phase extraction agent. Waste liquid is disposed of after being collected into a drain, a waste liquid collection container, or the like.

Next, the turntable 921, 1005 makes turn in a clockwise direction by an angle corresponding to one section so that C1 moves to the cartridge holding portion 904 positioned in the section D. The conditioning $H_2O$ dispensing mechanism 942 dispenses a certain amount of $H_2O$ to C1.

Subsequently, the turntable 921, 1005 makes turn in a clockwise direction by an angle corresponding to one section so that C1 moves to the cartridge holding portion 905 positioned in the section E. The pressure application mechanism 943 pressurizes C1, thereby causing the organic solvent to wet the solid-phase extraction agent. Waste liquid is disposed of after being collected into a drain, a waste liquid collection container, or the like.

Subsequently, the turntable 921, 1005 makes turn in a clockwise direction by an angle corresponding to one section so that C1 moves to the cartridge holding portion 906 positioned in the section F. The specimen dispensing mechanism 942 obtains a certain amount of specimen from a specimen container disposed at a specimen dispensing position of the specimen disposition mechanism 932, and dispenses the same to C1.

Subsequently, the turntable 921, 1005 makes turn in a clockwise direction by an angle corresponding to one section so that C1 moves to the cartridge holding portion 907 positioned in the section G. The internal standard substance dispensing mechanism 942 obtains a certain amount of internal standard substance from an internal standard substance container disposed at an internal standard substance dispensing position of the internal standard substance disposition mechanism 933, and dispenses the same to C1.

Next, the turntable 921, 1005 makes turn in a clockwise direction by an angle corresponding to one section so that C1 moves to the cartridge holding portion 908 positioned in the section H. The agitation mechanism 944 agitates the specimen and the internal standard substance in C1.

Subsequently, the turntable 921, 1005 makes turn in a clockwise direction by an angle corresponding to one section so that C1 moves to the cartridge holding portion 909 positioned in the section I. The pressure application mechanism 943 pressurizes C1, thereby causing a mixed solution of the specimen and the internal standard substance to wet the solid-phase extraction agent. Waste liquid is disposed of after collected into a drain, a waste liquid collection container, or the like.

Subsequently, the turntable 921, 1005 makes turn in a clockwise direction by an angle corresponding to one section so that C1 moves to the cartridge holding portion 910 positioned in the section J. The washing liquid dispensing mechanism 942 dispenses a certain amount of washing liquid to C1.

Subsequently, the turntable 921, 1005 makes turn in a clockwise direction by an angle corresponding to one section so that C1 moves to the cartridge holding portion 911 positioned in the section K. The pressure application mechanism 943 pressurizes C1, thereby causing the washing liquid to wet the solid-phase extraction agent. Waste liquid is disposed of after collected into a drain, a waste liquid collection container, or the like.

Subsequently, the turntable 921, 1005 makes turn in a clockwise direction by an angle corresponding to one section so that C1 moves to the cartridge holding portion 912 positioned in the section L. The eluent dispensing mechanism 942 dispenses a certain amount of eluent to C1.

Subsequently, the turntable 921, 1005 makes turn in a clockwise direction by an angle corresponding to one section so that C1 moves to the cartridge holding portion 913 positioned in the section M. The pressure application mechanism 943 pressurizes C1, thereby causing the washing liquid to wet the solid-phase extraction agent. FIG. 12 shows a side view of the system configuration in the section M. The eluent discharged from a solid-phase extraction cartridge 1001 (C1) is collected in a collection device 1002 which is provided at a position immediately below a discharge port. Further, in order to transfer the eluent to a mass spectrometry step, the eluent is provided to the MS unit 936, 1007 in an on-line or off-line manner to quantitate a target component in the eluent while separating the same from the eluent.

Examples of the off-line sample provision to the MS unit include a sample provision mechanism 939, 1009, for example, that aspirates and introduces a required amount of sample directly or indirectly (for example, a flow injection system) into an ion source of the MS unit, like the case of the separate type.

Subsequently, the turntable 921, 1005 makes turn in a clockwise direction by an angle corresponding to one section so that C1 moves to the cartridge holding portion 914 positioned in the section N. The solid-phase extraction cartridge movement mechanism 941 collects C1 from the turntable 921 and disposes of the same into the cartridge disposal portion 935. Note that, as described above, the cartridge disposal portion 935 can also store the cartridge.

The foregoing is a sequence of operations performed on the turntable, and if the turntable 921, 1005 next makes turn in a clockwise direction by an angle corresponding to one section, the cartridge holding portion which is empty after disposal of C1 returns to the section A 951, and one cycle of the solid-phase extraction treatment is completed.

Note that, in the above description, like the case of the separate type, after C1 has moved to the cartridge holding portion 902 positioned at the section B, C2 is charged into an empty cartridge holding portion positioned at the section A, for example, as a new solid-phase extraction cartridge 1001. C2 causes the treatment for a second specimen to start with delay of one section (operation) behind C1. Third and subsequent specimens are treated in the same manner, following C2, and therefore the treatments for 14 specimens corresponding to the number of sections are sequentially performed in parallel on the turntable. Re-examination is also treated in the same manner.

In the above fifth and sixth embodiments, although all the 14 solid-phase extraction cartridges on the turntable are subjected to solid-phase extraction treatment in parallel, they correspond to independent operations individually. That is, this shows that collection containers for waste liquids and extraction liquids of at least two cartridges of a plurality of solid-phase extraction cartridges on the same platform (turntable), or collection devices integrated with the cartridges can be individually switched.

The present invention can perform solid-phase extraction treatments on a plurality of specimens in parallel, and can randomly analyze examination items and randomly analyze various specimens.

Further, the number of consumed solid-phase extraction cartridges is determined according to the number of times of the solid-phase extraction treatment. This means that, unlike conventional plate-type high-throughput solid-phase extraction, a random high-throughput parallel solid-phase extraction treatment required in clinical analysis can be achieved, and, since an unused solid-phase extraction cartridge does not occur, a system with high cost-efficiency performance can be provided.

Descriptions of Reference Numerals

101, 201, 401, 501, 601: Solid-phase examination cartridge

102, 202, 402, 502, 602: Solid-phase examination column

103, 203, 403, 503, 603: Extraction agent

104, 204, 301, 404, 504, 604: Collection device (Tray mechanism)

105, 205, 302, 405, 505, 605: Waste liquid disposal section

106, 206, 303, 406, 506, 606: Extracted matter collection tank

107, 207, 304, 407, 507, 607: Narrow opening for pressure relief

108, 208, 408, 508, 608: Pressure holding valve

109, 209, 509, 609: Solid-phase column discharge port

210: Valve

305: Extracted matter collection tank—A

306: Extracted matter collection tank—B

409: Positioning structure

410: Turntable

411: Insertion portion for solid-phase extraction column

510: Cuvette
511: Light source
512: Photometric detection system
610: Narrow opening (introduction of pressure, sample, reagent, etc.)
611: Check valve—A
612: Check valve—B
613: Check ball
701: Solid-phase extraction column (Insertion portion)
702: Pressure application unit
703: Turntable for the part of a solid phase extraction column
704: Solid-phase extraction treatment unit
705: Waste liquid and extracted matter collection unit (of a type that has a small number of collection devices)
706: Waste liquid and extracted matter collection unit (of a type that has a large number of collection devices)
707: Waste liquid and extracted matter collection unit (of a type that has three vertices of collection devices)
708: Waste liquid and extracted matter collection unit (of a type that has collection devices in series)
709: Waste liquid and extracted matter collection unit (of an oval type)
710: Waste liquid and extracted matter collection unit (of a belt-conveyer type)
901: Cartridge holding portion positioned at section A
902: Cartridge holding portion positioned at section B
903: Cartridge holding portion positioned at section C
904: Cartridge holding portion positioned at section D
905: Cartridge holding portion positioned at section E
906: Cartridge holding portion positioned at section F
907: Cartridge holding portion positioned at section G
908: Cartridge holding portion positioned at section H
909: Cartridge holding portion positioned at section I
910: Cartridge holding portion positioned at section J
911: Cartridge holding portion positioned at section K
912: Cartridge holding portion positioned at section L
913: Cartridge holding portion positioned at section M
914: Cartridge holding portion positioned at section N
921, 1005: Turntable
931: Solid-phase extraction cartridge stock mechanism
932: Specimen disposition mechanism
933: Internal standard substance disposition mechanism
934, 1006: Collection container disposition mechanism
935: Solid-phase extraction cartridge disposal portion
936, 1007: MS unit
937: PC for control/computation
938, 1008: Monitoring mechanism
939, 1009: Sample provision mechanism
941: Solid-phase extraction cartridge movement mechanism
942: Dispensing mechanism
943, 1004: Pressure application mechanism
944: Agitation mechanism
951: Section A (Position where a solid-phase extraction cartridge is installed)
952: Section B (Position where conditioning organic solvent is dispensed)
953: Section C (Position where pressure is applied to cause wetting of conditioning organic solvent)
954: Section D (Position where conditioning $H_2O$ is dispensed)
955: Section E (Position where pressure is applied to cause wetting of conditioning $H_2O$)
956: Section F (Position where specimen is dispensed)
957: Section G (Position where internal standard substance is dispensed)
958: Section H (Position where specimen and internal standard substance are agitated)
959: Section I (Position where pressure is applied to cause wetting of sample solution)
960: Section J (Position where washing liquid is dispensed)
961: Section K (Position where pressure is applied to cause wetting of washing liquid)
962: Section L (Position where eluent is dispensed)
963: Section M (Position where pressure is applied to cause wetting of eluent)
964: (Position where a solid-phase extraction cartridge is disposed of)
1001: Solid-phase extraction cartridge
1002: Collection container (Collection device)
1003: Section M

The invention claimed is:

1. A biological sample pretreatment apparatus comprising:
a cartridge capable of holding an extraction agent for solid-phase extraction;
a solid-phase extraction cartridge holding unit capable of holding a plurality of the cartridges;
a first tray mechanism that receives a sample extracted from one of the cartridges at a predetermined first position on the holding unit, where
the first tray mechanism includes a plurality of sections, and a section switching mechanism that switches the sections to receive the sample extracted from the cartridge is provided; and
a second tray mechanism that receives extraction or sample liquids from a cartridge that is at a second position different from the first position on the holding unit, wherein the sections of the first tray mechanism can be switched independently of the second tray mechanism extraction operation.

2. The biological sample pretreatment apparatus according to claim 1, wherein the section switching mechanism is a mechanism that switches flow passages.

3. The biological sample pretreatment apparatus according to claim 1, wherein the section switching mechanism is a mechanism that moves a tray.

4. The biological sample pretreatment apparatus according to claim 1, wherein the first tray mechanism and the cartridge are integrated with each other.

5. The biological sample pretreatment apparatus according to claim 3, wherein the mechanism that moves a tray is a mechanism that rotates a tray.

6. The biological sample pretreatment apparatus according to claim 3, wherein the switching section mechanism moves or slides the first tray mechanism.

7. The biological sample pretreatment apparatus according to claim 5, wherein a solution discharge port that receives the sample extracted from the cartridge is deviated from a center of a bottom face of the cartridge.

8. The biological sample pretreatment apparatus according to claim 1, wherein the section switching mechanism is installed in another part of an apparatus main body.

9. The biological sample pretreatment apparatus according to claim 2, wherein the section switching mechanism switches flow passages and is a valve mechanism installed in a solution discharge port that receives the sample extracted from the cartridge.

10. The biological sample pretreatment apparatus according to claim 9, wherein the valve mechanism is installed in another part of an apparatus main body.

11. The biological sample pretreatment apparatus according to claim 4, further comprising:

a pressure relief mechanism that relieves pressure in the cartridge capable of holding the extraction agent for solid-phase extraction.

12. The biological sample pretreatment apparatus according to claim 1, further comprising:
a plurality of said cartridges and a plurality of said first tray mechanisms; and
a collection target switching mechanism that switches the receiving sections for at least two of the cartridges for use between waste liquid collection and extracted sample collection independently.

13. A mass spectrometer comprising the biological sample pretreatment apparatus according to claim 12.

* * * * *